United States Patent [19]

Yoshimoto et al.

[11] Patent Number: 4,612,371
[45] Date of Patent: Sep. 16, 1986

[54] ANTHRACYCLINE ANTIBIOTICS

[75] Inventors: Akihiro Yoshimoto; Shizuka Fujii; Katsuro Kubo, all of Fujisawa; Tomoyuki Ishikura, Chigasaki; Tsutomu Sawa, Ayase; Tomio Takeuchi; Hamao Umezawa, both of Tokyo, all of Japan

[73] Assignee: Sanraku Incorporated, Tokyo, Japan

[21] Appl. No.: 756,876

[22] Filed: Jul. 18, 1985

[30] Foreign Application Priority Data

Jul. 25, 1984 [JP] Japan .................................. 59-155950

[51] Int. Cl.$^4$ ........................................... C07H 15/24
[52] U.S. Cl. ................................................... 536/6.4
[58] Field of Search ............................ 536/6.4; 514/34

[56]  References Cited
U.S. PATENT DOCUMENTS 4,144,329  3/1979  Umezawa et al. .................... 536/6.4
4,188,377  2/1980  Suarato et al. ........................ 536/6.4

Primary Examiner—Johnnie R. Brown
Assistant Examiner—Elli Peselev
Attorney, Agent, or Firm—Frank J. Jordan; C. Bruce Hamburg; Manabu Kanesaka

[57] ABSTRACT

Novel anthracycline antibiotics characteristic of Ring A of the anthracycline skeleton are produced by microorganisms belonging to the genus Streptomyces and are useful as anti-cancer agents. The antibiotics designated D-788-6 to -10 are shown by general formula:

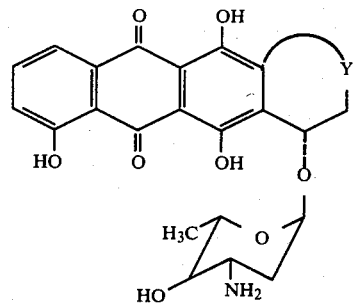

wherein Y represents a group shown by:

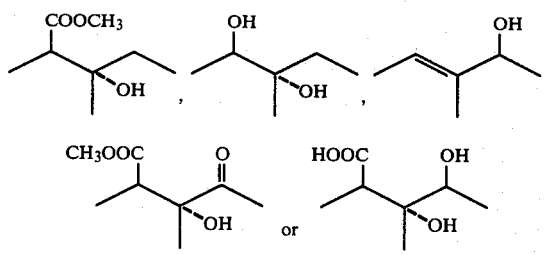

6 Claims, No Drawings

ANTHRACYCLINE ANTIBIOTICS

BACKGROUND OF THE INVENTION

1. Field of the Invention

The present invention relates to novel anthracycline antibiotics which are produced by microorganisms belonging to the genus Streptomyces.

2. Description of the Prior Art

As anthracycline type antibiotics, daunomycin (cf. U.S. Pat. No. 3,616,242) and adriamycin (cf. U.S. Pat. No. 3,590,028), obtained from a culture solution of actinomycetes have been hitherto known. These compounds exhibit a broad anti-cancer spectrum against experimental tumors and have been widely utilized as chemotherapic agents against cancers also from a clinical aspect. However, the anti-cancer action of daunomycin and adriamycin is not necessarily satisfactory though they show a considerably potent action. Thus, attempts to produce various compounds analogous thereto have been made by various means of fermentation, semi-synthesis, conversion using microorganisms and, some anthracycline antibiotics have already been proposed (for example, Published Examined Japanese Patent Application No. 34915/76 aclacinomycins A and B), T. Oki et al, The Journal of Antibiotics, vol. 33, pages 1331–1340, F. Areamone, Topics in Antibiotic Chemistry, vol. 2, pages 102–279, published by Ellis Horwood Limited, Published Unexamined Japanese Patent Application No. 56494/82 (4-demethoxy-11-deoxydaunomycin, etc.), Published Unexamined Japanese Patent Application No. 15299/81 (rhodomycin series antibiotics), etc. are disclosed).

As anthracycline antibiotics as anti-cancer agents, a variety of analogous compounds have been proposed as described above; a part of them has been widely used for clinical purpose and provided for clinical test.

However, none of them is satisfactory both in toxicity and anti-cancer action. Further, results of anti-tumor agents obtained with in vitro tests and animal tests are not always reflective directly on anti-cancer action against human and therefore, investigations are required from various viewpoints. For this reason, it has been desired to propose compounds belonging to a further new class, with respect to anthracycline antibiotics which have been evaluated in a way.

SUMMARY OF THE INVENTION

An object of the present invention is to provide novel anthracycline antibiotics represented by formula:

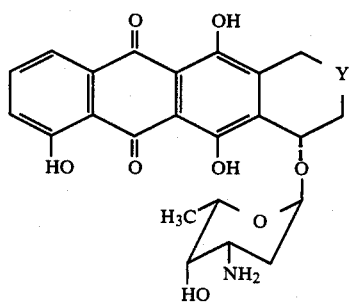

wherein Y represents a group shown by:

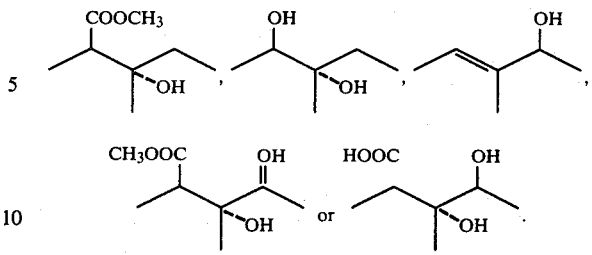

These compounds possess a highly inhibiting action against proliferation of cultured mouse leukemia cell L 1210 and are useful against L 1210 leukemia in mice.

DETAILED DESCRIPTION OF THE INVENTION

The present invention provides novel anthracycline antibiotics represented by formula:

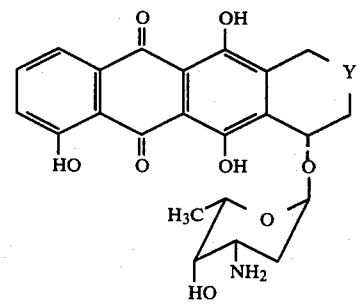

wherein Y represents a group shown by:

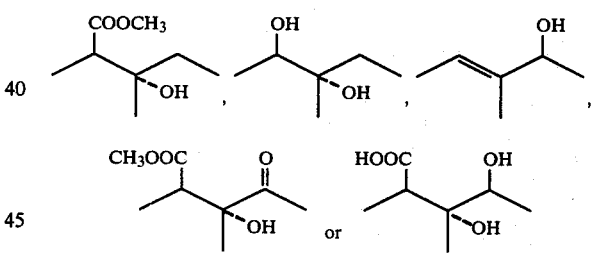

These compounds are novel antibiotics unknown by any publication which are structurally characteristic of ring A of the anthracyclinone skeleton. Hereafter, among compounds shown by formula (I), an antibiotic represented by formula:

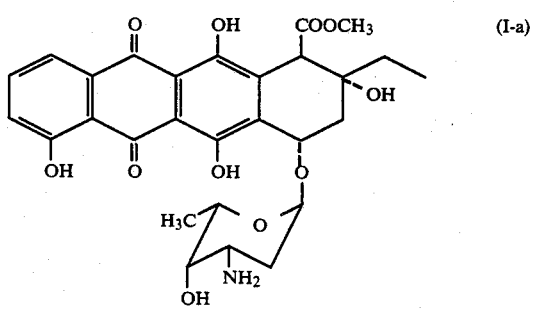

is designated D788-6;

an antibiotic represented by formula:

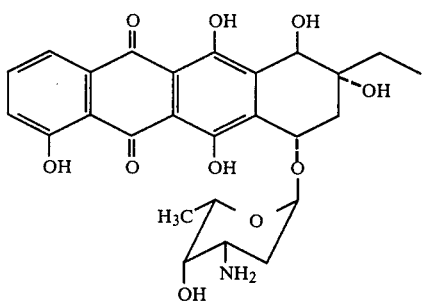

is designated D788-7;
an antibiotic represented by formula:

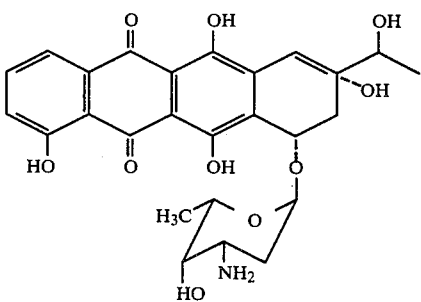

is designated D788-8;
an antibiotic represented by formula:

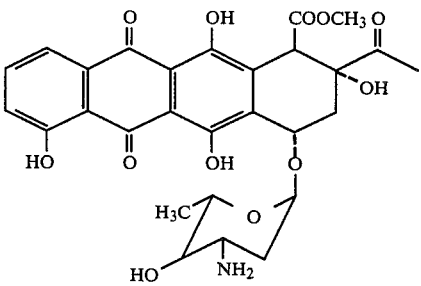

is designated D788-9; and
an antibiotic represented by formula:

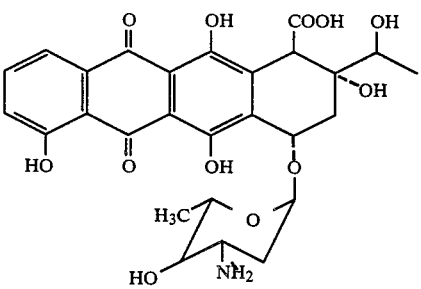

is designated D788-10.

These compounds exhibit a highly inhibitory action against proliferation of cultured mouse leukemia cell L 1210 and are per se useful against L 1210 leukemia in mice. INHIBITORY ACTION AGAINST PROLIFERATION OF MOUSE L 1210 LEUKEMIA CELL AND AGAINST SYNTHESIS OF NUCLEIC ACID L 1210 cells of $5 \times 10^4$/ml were inoculated on, e.g., RPM 11640 medium (Rosewellberg Research Laboratories) containing 20% bovine serum and, the substances of the present invention were added thereto, respectively, in a concentration of 0.02 to 0.25 μg/ml in a similar fashion. Cultivation was performed at 37° C. in a carbon dioxide culture bottle. Then, a 50% inhibitory action against proliferation was determined based on control fraction. Further, the aforesaid L 1210 culture cell was suspended in 10% bovine serum-containing RPM 11640 medium in a concentration of $5 \times 10^5$/ml. After cultivating at 37° C. for 1 to 2 hours in a carbon dioxide culture bottle, the substance was added in various concentrations and, $^{14}$C-uridine (0.05 μCi/ml) or $^{14}$C-thymidine (0.05 μCi/ml) was further added thereto 15 minutes after followed by culturing at 37° C. for 60 minutes. A cold 10% trichloro-acetic acid was added to the reaction solution to discontinue the reaction and at the same time, matters insoluble in the acid were precipitated. After washing further twice with cold 5% trichloroacetic acid, the insoluble matters were dissolved in formic acid and, radioactivity was measured. A 50% intake inhibitory concentration was determined from an intake rate of radioactivity, based on the control fraction to which no substance was added. The results are shown in Table 1.

TABLE 1

Inhibitory Action of Compounds of this Invention against Proliferation of Mouse Leukemia L1210 Culture Cell and against Synthesis of Nucleic Acid

| | 50% Inhibitory Concentration ($IC_{50}$) (μg/ml) | | |
|---|---|---|---|
| | Inhibition of Cell Proliferation | Inhibition of DNA Synthesis | Inhibition of RNA Synthesis |
| D788-6 | 0.25 | 2.6 | 1.30 |
| D788-7 | 0.0003 | 0.29 | 0.68 |
| D788-8 | 0.22 | 3.4 | 1.58 |
| D788-9 | 0.22 | 4.2 | 2.59 |
| D788-10 | 0.083 | 10 | 10 |

The anti-tumor activity against mouse L 1210 leukemia is shown in Table 2.

TABLE 2

In vivo Anti-Tumor Activity of D788-7 against Mouse L1210 Leukemia
Anti-Tumor Activity in vivo

| Dose (μg/kg/day) | Anti-tumor Effect T/C(%) |
|---|---|
| 250 | 100 |
| 125 | 172 |
| 62.5 | 204 |
| 32 | 187 |
| 16 | 133 |
| 8 | 104 |
| 4 | 102 | mice: CDF1 n = 6
Inoculation: $1 \times 10^5$ cell/mouse (i.p.)
Treatment: day 1 to day 10 (i.p.)

The foregoing anthracycline antibiotics can be produced by culturing in a medium comprising suitable nutrient sources a strain producing the product of the present invention which is easily isolated by a conventional variation treatment of a strain belonging to the genus Actinomyces and capable of producing daunomycin and analogous compounds thereto which is isolated from the soil or is known, using as a variant, for example, N-methyl-N'-nitro-N-nitrosoquanidine (NTG). Among these producing strains, a specific example includes an RPM-5 strain which is a variant obtained by a variation treatment of Streptomyces D 788 strain producing daunomycin and paumycin, which is newly isolated from the soil, with NTG.

This strain has been deposited on July 2, 1984 at the Fermentation Research Institute, Agency of Industrial Sciences and Technology under the international deposit accession No. 811 (FERM BP-811).

Hereafter, the bacteriological properties of the RPM-5 strain are described below.

(i) Morphology

Linear aerial mycelium is developed from branching substrate mycelia but no whirle is formed. Matured spores in a chain of 10 or more have a diameter of about 0.6 to 0.8×0.9 to 2.5 microns. The spores have smooth surfaces. Neither ascospore nor flagella spore is formed.

(ii) Growth conditions in various media

With respect to color indication, standard shown within parenthesis is based on "System of Color Wheels for Streptomycete Taxonomy" written by Tresner & E. J. Backus (J. Appl. Microbiol., vol. 11, pages 335-338, 1963), which is supplemented by "Color Standard" published by Nippon Color Research Laboratories.

(iii) Physiological characteristics (1) Growth temperature range: (tested at each temperature of 20° C., 28° C., 30° C., 37° C. and 42° C. at pH 6.0 using yeast-maltoseagar medium) Grow at each temperature of 20° to 37° C. but cannot grow at 42° C.

(2) Liquefaction of gelatin: positive (cultured at 20° C. using glucosepeptone-gelatin medium)

(3) Hydrolysis of starch: positive (starch-inorganic salt-agar medium)

(4) Coagulation of skim milk and peptonization: all negative at the initial stage but 15 days after cultivation, peptonization started.

(5) Formation of melanine-like pigment: (using tryptone-yeast-broth, peptone-yeast-iron-agar and tyrosine-agar media) positive in all media

(iv) Utilization of various carbon sources: (Pridham-Gottlieb agar medium)

1. L-Arabinose: positive
2. D-Xylose: positive
3. D-Glucose: positive
4. D-Fructose: positive
5. Sucrose: positive
6. Inositol: positive
7. L-Rhamnose: negative
8. Raffinose: negative
9. D-Mannitol: positive Cultivation of producing bacteria relating to the present invention can be performed in medium compositions which are ordinarily used as nutrient sources for actinomycetes and are per se known. For example, as carbon sources, there can be used glucose, glycerine, sucrose, starch, maltose, animal and vegetable oils, etc.; as nitrogen sources, there can be used, for example, organics such as soybean powders, meat extract, yeast extract, peptone, corn steep liquor, cotton seed lees, fish powders, etc. and inorganic nitrogens such as ammonium sulfate, ammonium chloride, sodium nitrate, ammonium phosphate, etc. If necessary and desired, sodium chloride, potassium chloride, phosphates or bivalent metals salts such as $Mg^{++}$, $Ca^{++}$, $Zn^{++}$, $Fe^{++}$, $Cu^{++}$, $Mn^{++}$, or $Ni^{++}$, etc and amino acids or vitamins can be added. In addition, for purpose of preventing foaming during fermentation, defoaming agents, for example, silicone (made by Shin-Etsu Kagaku K. K., -KM 75, trademark), etc. can be appropriately added.

Conditions for fermentation such as temperature, pH, aerial agitation and a time period for the fermentation, etc. may be chosen in such a manner that the bacteria used accumulates the maximum amount of the compound. For example, it is advantageous to perform the fermentation at temperatures of 20° to 40° C., preferably at 28° C., at pH of 5 to 9, preferably 6 to 7, for a time period for the fermentation of 1 to 10 days, preferably 6 days.

To isolate and collect the substances D788-6 to 10 from the culture solution, the culture solution after completion of the fermentation is subjected to centrifugal separation or filtered in the presence of a suitable filtering aid such as diatomaceous earth thereby to separate into the bacteria and the supernatant or the filtrate. The substances are extracted from the supernatant with organic solvents such as chloroform, toluene, ethyl acetate, etc. at pH of 7 to 9.

From the bacteria, the substances are extracted, if necessary and desired, using organic solvents such as acetone, methanol, ethanol, butanol, etc. Each of the extracts is concentrated to dryness to obtain red, crude powders. The powders are treated with chromatography using adsorption carriers, for example, synthetic adsorbing resins or silica gel, or, treated with anionic ion exchange resins and cationic ion exchange resins, singly or in suitable combination, to harvest each of substances D788-6 to 10 in a pure form.

Hereafter, the present invention will be described in more detail, referring to the examples below.

EXAMPLE 1

From an YS (0.3% yeast extract, 1% soluble starch, 1.5% agar, pH 7.2) slant culture solution of Streptomyces D 788, RPM-5 strain (deposited in Fermentation Research Institute, Agency of Industrial Science and Technology under the accession No. 7703), a platinum loop was taken out and inoculated in a 500 ml volume Erlenmeyer's flask in which 100 ml aliquot of a seed culture medium described below was charged and sterilized. Shake culture was performed at 20° C. for 2 days in a rotary shaker (220 rpm) to prepare a seed culture.

Seed culture medium:
Soluble starch: 0.5%
Glucose: 0.5%
Esusan Meat (soybean powder, made by Ajinomoto Limited): 1.0%
Yeast extract: 0.1%
Sodium chloride: 0.1%
Potassium secondary phosphate: 0.1%
Magnesium sulfate (containing $7H_2O$): 0.1 %
Tap water: pH 7.4 (before sterilization)

Then, 15 liters of a production medium having a composition described below were charged in a 30 liter-volume jar fermentor and then sterilized. Then, and, 750 ml (corresponding to 5%) each of the aforesaid seed culture solution was added thereto and inoculated.

Production medium:
Taiwan yeast: 5%
Soluble starch: 7.5%
Yeast extract: 0.2%
Sodium chloride: 0.2%
Calcium carbonate: 0.3%
Mineral mixture*: 0.06%
Tap water: pH 8.2 (before sterilization)

*A solution of 2.8 g of $CuSO_4.5H_2O$, 0.4 g of $FeSO_4.7H_2O$, 3.2 g of $MnCl_2.4H_2O$ and 0.8 g of $ZnSO_4.2H_2O$ in 500 ml of distilled water.

When cultivation was performed at 28° C. for 130 hours are an aerial amount or 15 l./min. while agitating at 45 rotations/min., the culture solution became a deep red brown color because of the product. The culture solution was collected from the jar fermentor. The pH of the culture solution was rendered 1.7 with conc. sulfuric acid followed by agitation at room temperature for about 1 hour. To the culture solution was added 2% of a filtering aid and the bacteria was separated by filtration to obtain 13.5 liters of the filtrate. Further, the bacterial fraction was suspended in 6 liters of acetone followed by agitating for 20 minutes and extraction. After filtering, the acetone extract was taken and concentrated to about 1.5 liters under reduced pressure. The concentrate was combined with the previously obtained filtrate to make 15 liters.

The aforesaid filtrate (pH was adjusted to 2.0 to 2.5 with 4N sodium hydroxide) was passed through a column packed with 750 ml of Dia Ion HP-20 (synthetic absorbing resin, made by Mitsubishi Chemical Co., Ltd.) at SV of 4.5 to absorb the product. Thereafter, washing with 1.5 liters of water having pH 1.7 (dil. sulfuric acid) was performed and then the absorbed matter was eluted with 1.4 liters of 50% acetone water (pH 1.7). The eluate was concentrated under reduced pressure to about 800 ml. Then, the concentrate was adjusted to pH of 8.5 with 4N sodium hydroxide and extracted with chloroform (2 liters in total). The thus obtained chloroform extract was washed with water and then a saturated sodium chloride aqueous solution and dried over Glauber's salt. After Glauber's salt was filtered off, the filtrate was concentrated to a small quantity under reduced pressure. An excess of n-hexane was added to cause precipitation. The filtrate was collected by filtration and dried in vacuum to obtain 1.84 g of crude powders containing D788-6, D788-7, D788-8 and D788-9.

On the other hand, the residue remained after the extraction with chloroform was adjusted to pH of 2.5 with 6N hydrochloric acid and then extracted with n-butanol (1.5 liters in total). The thus obtained butanol extract was rinsed with water showing pH of 2.5. After butanol was removed by concentration under reduced pressure, the residue was dissolved in a small quantity of methanol. An excess of toluene was added to the solution to cause precipitation. The solvent was removed by distillation to obtain 5.0 g of crude powders containing D788-10.

EXAMPLE 2

In a column, 30 g of Wako Silica Gel C-200 (made by Wako Junyaku Kogyo Co., Ltd.) was packed with a chloroform-methanol (20:1) mixture. The crude powders, 600 mg, obtained by extraction with chloroform in Example 1 were dissolved in a small quantity of a chloroform-methanol (20:1) mixture and the solution was adsorbed to the upper layer of the silica gel column followed by development with the same solvent system. After aglycon eluted out earlier was removed, development was performed with 160 ml of a chloroform-methanol (15:1) mixture, 140 ml of the same (13:1) mixture and then 260 ml of the same (12:1) mixture to elute a D788-6 fraction. Further, 200 ml of a chloroform-methanol (10:1) mixture was flown down to elute a fraction containing D788-9. Then, elution was performed with 200 ml of a chloroform-methanol-water (200:20:0.5) mixture and then 200 ml of the same (180:20:1) mixture to obtain a fraction containing D788-7 and D788-8. The weight of the crude powders in each fraction obtained by concentration to dryness was as follows.

D788-6 Fraction: 21 mg
D788-7 Fraction: 45 mg
D788-8 Fraction: 79 mg
D788-9 Fraction: 85 mg Each of the crude powders described above was purified by thin layer chromatography for fractionation, as described below.

D788-6: The aforesaid D788-6 fraction was purified using a silica gel thin layer (20×20 cm) (PF 254 Silica Gel, made by Merck Inc.) for fractionation. The fraction was spotted in a horizontal line shape at a location of 15 mm from the lower end of the thin layer followed by development with a chloroform-methanol-water (25:10:1) mixture. D788-6 bands were collected and extracted with a chloroform-methanol (8:1) mixture. After the extract was concentrated to dryness, the obtained powders were dissolved in a 0.1lM acetic acid buffer solution (pH 3.0) and the solution was extracted and washed with chloroform. After the aqueous phase remained after the extraction was adjusted with 4N sodium hydroxide to pH of 8.5, the aqueous phase was extracted with chloroform. After the resulting extract was washed with water and then with a saturated sodium chloride aqueous solution, it was dried over Glauber's salt. The chloroform extract was filtered and the filtrate was concentrated under reduced pressure. An excess of n-hexane was added to the concentrate to cause precipitation. The product was collected by filtration and dried in vacuum to obtain 10 mg of pure D788-6 substance.

D788-7: The aforesaid D788-7 fraction was subjected to thin layer chromatography of silica gel (supra) for fractionation using development solvent, chloroform-methanol-water-acetic acid (120:25:6:14). Bands corresponding to D788-7 were collected and extracted with a chloroform-methanol-water (4:1:0.5) mixture. After the extract was concentrated to dryness, the residue was dissolved in 0.1M acetic acid buffer (pH 3.0) and the solution was washed with chloroform and extracted with chloroform at pH of 8.5 in a manner similar to the purification of D788-6 described above to give 21 kg of pure D788-7 substance.

D788-8: The aforesaid D788-8 fraction obtained by silica gel column chromatography was purified by thin layer chromatography for fractionation (supra) using development solvent, chloroform-methanol-water-acetic acid-28% ammonia water (125:55:5.5:0.9 : 1.1). Bands corresponding to D788-8 were collected and extracted with a chloroform-methanol-water (4:1:0.5) mixture. Subsequently, the extract was treated in a manner similar to the purification of the D788-6 fraction described above to give 28 mg of pure D788-8.

D788-9: The D788-9 fraction (80 mg) obtained by silica gel chromatography described above was subjected to a column filled up with a suspension of 4 g of Wako Silica Gel C-200 (supra) in a chloroform-methanol (20:1) mixture and again subjected to chromatography developing with the same solvent system to obtain D788-9 having a purity of about 50%. This was further subjected to thin layer chromatography for fractionation (supra) and developed with development solvent, a chloroform-methanol-water-acetic acid (120:25:6:14) mixture to separate and purify. Bands corresponding to D788-9 were collected and extracted with a chloroform-methanol-water (4:1:0.5) mixture. Subsequently, the extract was treated in a manner similar to D788-6 described above to give 22 mg of pure D788-9.

EXAMPLE 3

The crude powders (5 g) extracted with butanol containing D788-10 obtained in Example 1 were subjected to a column prepared by filling up with a suspension of 35 g of Wako Silica Gel C-200 (supra) in chloroform-methanol-water (100:10:0.5) and then developed, in sequence, with 200 ml of a chloroform-methanol-water (90:10:1) mixture, 360 ml of the same (80:10:1) mixture, 240 ml of the same (70:10:1) mixture and then 210 ml of the same (60:10:1) mixture to obtain further purified D788-10 fractions. The D788-10 fractions were collected and concentrated under reduced pressure to obtain partly purified D788-10 powders. The powders were dissolved in a diluted sodium hydrogen carbonate aqueous solution. After the solution was washed with chloroform and the remained aqueous phase was adjusted to pH of 2.5 with 6N hydrochloric acid, the aqueous phase was extracted with n-butanol. The extract was concentrated under reduced pressure to obtain 80 g of powders. The powders were further purified by thin layer chromatography for fractionation using development solvent, chloroform-methanol-water acetic acid-28% ammonia water (125:55:5.5:0.9:1.1). Fractions corresponding to D788-10 were collected and extracted with a mixture obtained by adding a drop of acetic acid to chloroform-methanol-water (4:10.5). After the extract was concentrated under reduced pressure, the residue was dissolved in a diluted sodium hydrogen carbonate aqueous solution. After the solution was washed with chloroform, the solution was adjusted to pH of 2.5 with 6N hydrochloric acid and then extracted with n-butanol. The extract was concentrated to dryness to obtain 32 mg of purified D788-10 substance. Physico-chemical properties of each of the substances obtained in the above examples are shown below.

D788-6

(A) melting point 138–140° (decomposed).
(B) $[\alpha]_D^{25} + 165°$ C. (c=0.015, methanol).
(C) UV and visible absorption spectra (methanol): λmax num ($E_{1\,cm}^{1\%}$): 206 (311), 235 (647), 255 (403), 290 (141), 492 (229), 511sh (177), 527sh (153).
(D) IR absorption spectrum (KBr) $\gamma cm^{-1}$: 1720, 1590, 1450, 1420, 1390, 1280, 1270, 1190, 1160, 1000, 980.
(E) $^1$H-NMR spectrum (CDCl$_3$) δppm: 1.1 (3H, t, J=7.5 H-14); 1.33 (3H, d, J=6.5 H-6'), 1.51 (1H, dd, J=12.4 H-2'a), 1.6-2.1 (3H, m, H-13, H-2'b); 2.1-2.4 (2H, m, H-8); 3.05 (1H, dd, J=11.4 H-3'); 3.41 (1H, bs, H-4'); 3.69 (3H, s, COOCH$_3$); 4.1 (1H, q, J=6.5 H-5'); 4.26 (1H, s, H-10); 5.22 (1H, bs, H-7); 5.43 (1H, bs, H-1'); 7.22 (1H, dd, J=8.2 H-3); 7.62 (1H, t, J=8 H-2); 7.71 (1H, dd, J=8.2 H-1);

D788-7

(A) melting point 165°–167° C.
(B) $[\alpha]_D^{25} + 16°$ (c=0.0125, methanol).
(C) UV and visible absorption spectra (in methanol) $\lambda_{max}^{CH_3OH}$ nm ($E_{1\,cm}^{1\%}$): 207 (332), 235 (702), 254 (424), 292 (139), 492 (254), 512sh (187), 528 (169).
(D) IR absorption spectrum (KBr) $\alpha cm^{-1}$: 1595, 1450, 1430, 1400, 1290, 1230, 1190, 1160, 1110, 1005, 980.
(E) $^1$H-NMR spectrum (CDCl$_3$+CD$_3$OD) δppm: 1.09 (3H, t, J=7.5 H-14); 1.32 (3H, d, J=6.5 H-6'); 1.6–1.9 (4H, m, H-2', H-13); 2.2 (2H, bs, H-8); 2.7-3.2 (1H, m, H-3'); 3.46 (1H, bs, H-4'); 4.12 (1H, q, J=6.5 H-5'); 4.81 (1H, s, H-10); 5.1 (1H, bs, H-7); 5.4 (1H, bs, H-1'); 723 (1H, dd, J=8, 1.5 H-3); 7.64 (1H, t, J=8 H-2); 7.79 (1H, dd, J=8, 1.5 H-1).

D788-8

(A) melting point 126°–128° C. (decomposed).
(B) $[\alpha]_D^{25} + 309°$ (c=0.0175, methanol).
(C) UV and visible absorption spectra (in methanol): $\lambda_{max}^{CH_3OH}$ nm ($E_{1\,cm}^{1\%}$): 206 (609), 227 (429), 269 (619), 494 (283), 515 (300), 550sh (183).
(D) IR absorption spectrum (KBr) $\gamma cm^{-1}$: 1600, 1460, 1400, 1370, 1285, 1250, 1200, 1170, 1110, 1015, 980.
(E) $^1$H-NMR spectrum (CDCl$_3$-CD$_3$OD) δppm: 1.3 (1H, d, J=6.5 H-6'); 1.4 (3H, d, J=6.5 H-14); 1.5–1.9 (2H, m, H-2'); 2.5 (1H, dd, J=18, 4.5 H-8a); 2.8 (1H, d, J=18 H-8b); 2.8-3.2 (1H, m, H-3'); 3.38 (1H, bs, H-4'); 3.98 (1H, q, J=6.5 H-5'); 4.49 (1H, q, J=6.5 H-13); 5.2 (1H, bs, H-1'); 6.97 (1H, bs, H-10); 7.18 (1H, dd, J=8 1.5 H-3); 7.59 (1H, t, J=8 H-2); 7.75 (1H, dd, J=8, 1.5 H-1).

D788-9

(A) melting point 175°–180° C.
(B) $[\alpha]_D^{25} + 62°$ (c=0.0145, methanol).
(C) UV and visible absorption spectra (in methanol): $\lambda_{max}^{CH_3OH}$ nm($E_{1\,cm}^{1\%}$): 206 (307), 235 (671), 255 (428), 291 (153), 481sh (212), 493 (226), 512sh (171), 526 (148).
(D) IR absorption spectrum (KBr) $\gamma cm^{-1}$: 1725, 1710sh, 1600, 1450, 1430, 1400, 1290, 1240, 1190, 1165, 1110, 1005, 980.
(E) $^1$H-NMR spectrum (CDCl$_3$) δppm: 1.36 (3H, d, J=6.5 H-6'); 1.5–2.0 (2H, m, H-2'); 2.2 (1H, dd, J=16, 4.5 H-8a); 2.27 (3H, s, H-14); 2.6 (1H, d, J=16 H-8b); 2.9–3.3 (1H, m, H-3'); 3.46 (1H, bs, H-4'); 3.69 (3H, s, COOCH$_3$); 4.13 (1H, q, J=6.5 H-5'); 4.37 (1H, s, H-10); 5.12 (1H, d, J=4.5 H-7); 5.42 (1H, bs, H-1'); 7.23 (1H, dd, J=8, 1.5 H-3); 7.6 (1H, t, J=8 H-2); 7.77 (1H, dd, J=8, 1.5 H-1).

D788-10

(A) melting point 174°–176° C.
(B) $[\alpha]_D^{25} + 200°$ (c=0.0185, methanol).
(C) UV and visible absorption spectra (in methanol): $\lambda_{max}^{CH_3OH}$ nm($E_{1\,cm}^{1\%}$): 209 (362), 226 (371), 257 (329), 497 (169), 514sh (155).
(D) IR absorption spectrum (KBr) $\gamma cm^{-1}$: 1710, 1600, 1450, 1390, 1280, 1230, 1190, 1160, 1115, 1010, 980.
(E) $^1$H-NMR spectrum (CDCl$_3$-CD$_3$OD) δppm: 1.3 (3H, d, J=6.5 H-6'); 1.4 (3H, d, J=6.5 H-14); 1.5–1.9 (2H, m, H-2'); 2.1–2.8 (2H, m, H-8); 3.7 (1H, bs, H-4'); 4.0 (1H, q, J=6.5 H-13); 4.1 (1H, s, H-10); 4.2 (1H, q, J=6.5 H-5'); 5.1 (1H, bs, H-7); 5.5 (1H, bs, H-1'); 7.2 (1H, dd, J=8, 1.5 H-3); 7.6 (1H, t, J=8 H-2); 7.7 (1H, dd, J=8, 1.5 H-1).

While the invention has been described in detail with reference to specific embodiments thereof, it will be apparent to one skilled in the art that various changes and modifications can be made therein without departing from the spirit and scope thereof.

What is claimed is:

1. An anthracycline antibiotic represented by formula:

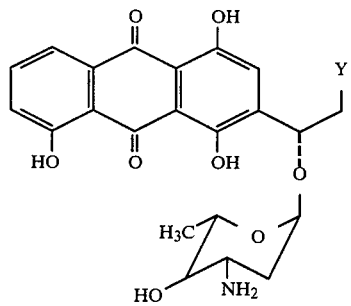

wherein Y represents a group shown by:

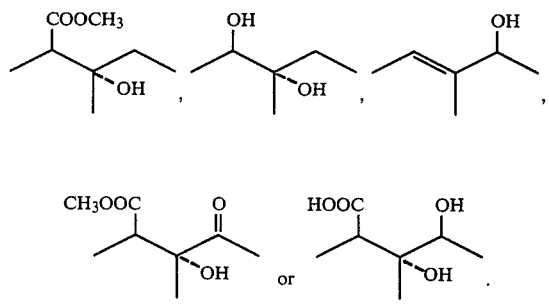

2. An anthracycline antibiotic according to claim 1 which is shown by formula:

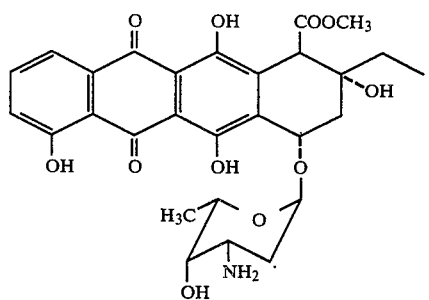

3. An anthracycline antibiotic according to claim 1 which is shown by formula:

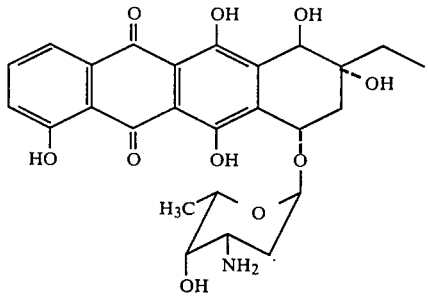

4. An anthracycline antibiotic according to claim 1 which is shown by formula:

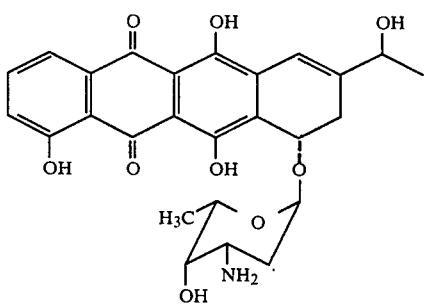

5. An anthracycline antibiotic according to claim 1 which is shown by formula:

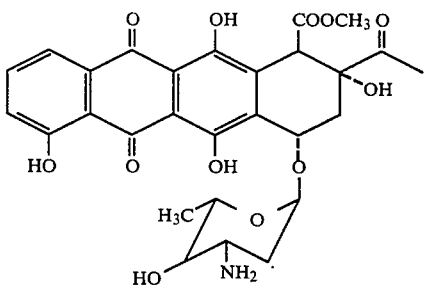

6. An anthracycline antibiotic according to claim 1 which is shown by formula:

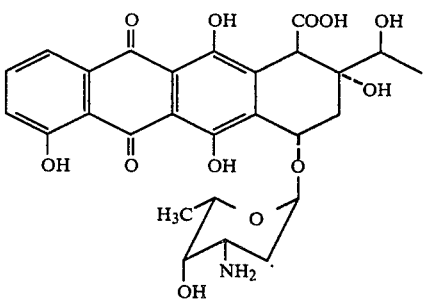

* * * * *